United States Patent [19]

Spang et al.

[11] Patent Number: 4,820,757
[45] Date of Patent: Apr. 11, 1989

[54] POLYMERS PHOTOSTABILIZED BY NOVEL IMIDAZOLE-2-CARBOXANILIDES

[75] Inventors: Peter Spang, St. Ingbert; Peter Neumann, Wiesloch; Gerhard Wagenblast, Frankenthal; Hubert Trauth, Dudenhofen, all of Fed. Rep. of Germany

[73] Assignee: BASF Aktiengesellschaft, Ludwigshafen, Fed. Rep. of Germany

[21] Appl. No.: 167,726

[22] Filed: Mar. 14, 1988

[30] Foreign Application Priority Data

Mar. 14, 1987 [DE] Fed. Rep. of Germany ....... 3708292

[51] Int. Cl.⁴ .............................................. C08K 5/34
[52] U.S. Cl. ...................................... 524/93; 524/103; 524/104; 524/106; 548/331; 548/343
[58] Field of Search .................. 548/343, 331; 524/93, 524/104, 106, 103

[56] References Cited

U.S. PATENT DOCUMENTS

| | | | |
|---|---|---|---|
| 3,205,083 | 9/1965 | Green | 524/106 |
| 3,637,584 | 1/1972 | Hurlock et al. | 524/106 |
| 3,661,925 | 5/1972 | McCaully et al. | 548/331 |
| 3,740,413 | 6/1973 | McCaully et al. | 548/331 |
| 3,907,700 | 9/1975 | Grier | 524/93 |
| 4,011,236 | 3/1977 | Grier | 548/306 |
| 4,017,508 | 4/1977 | Pond | 548/343 |
| 4,594,425 | 6/1986 | Musser et al. | 548/331 |

FOREIGN PATENT DOCUMENTS 1517719 3/1968 France.
1260294 1/1972 United Kingdom.

OTHER PUBLICATIONS

CA 101, 23395a (1987).
CA 98, 143322r (1983).
Rastogi et al: Indian J. Chem., vol. 18B, 464–467 (1979).
Gompper et al: Chem. Bericlite 92, 550–563 (1959).
G. Holan et al: J. Chem. Soc. (C)-25–29 (1967).
Robert Sallë et al.: Bull. de La Sociëtë Chemique de France, 3368–3369 (1966), No. 10.

*Primary Examiner*—Veronica P. Hoke
*Attorney, Agent, or Firm*—Oblon, Fisher, Spivak, McClelland & Maier

[57] ABSTRACT

Photostabilized polymers, including polyurethanes and plastics coatings, contain as photostabilizer one or more compounds of the formula

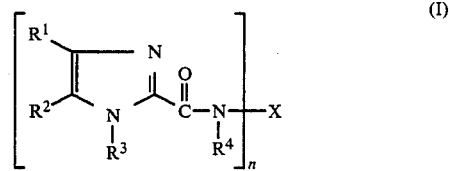

or a novel imidazole-2-carboxanilide of the formula

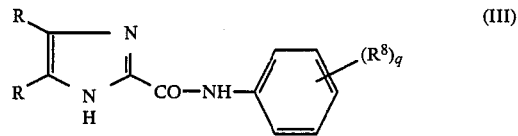

11 Claims, No Drawings

POLYMERS PHOTOSTABILIZED BY NOVEL IMIDAZOLE-2-CARBOXANILIDES

U.S. Pat. Nos. 3,907,700 and 4,011,236 disclose N-(benzimidazol-2-yl)arylcarboxamides of the formula (X)

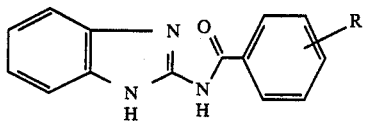

as UV stabilizers for organic polymers. However, these amides provide inadequate stabilization, for example in polyurethane. A further disadvantage is the incompatibility with many plastics, the volatility, and the discoloration of the polymeric substrates after incorporation of the amides.

It is an object of the present invention to provide compounds which have high absorption in the wavelength range 280-400 nm, low volatility and little tendency to discolor on thermal processing.

U.S. Pat. Nos. 3,740,413 and 3,661,925 disclose benzimidazole-2-carboxanilides as pharmaceutically active compounds. Further benzimidazole-2-carboxanilides and 4,5-diphenylimidazole-2-carboxanilides are described in French Patent No. 1,517,719, Chem. Ber. 92 (1959), 550, J. Chem. Soc. Sect. C 1967, 20, CA 101, 23395a and CA 98, 143322r.

We have found that the aromatic imidazole-2-carboxanilides of the invention meet this object and are highly suitable for photostabilizing organic materials.

The present invention accordingly provides a photostabilized polymer containing as photo-stabilizer one or more compounds of the general formula (I)

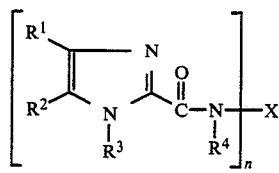

where
n is 1 or 2,
$R^1$ and $R^2$ or one of the radicals $R^1$ or $R^2$ are each independently of the other phenyl or hetaryl which each may be substituted by $C_1$-$C_{12}$-alkyl, $C_1$-$C_{12}$-alkoxy, phenoxy, halogen or trifluoromethyl, and the other of the radicals $R^1$ or $R^2$ is hydrogen, $C_1$-$C_{12}$-alkyl, $C_7$-$C_9$-phenalkyl or —COOR$^5$, where $R^5$ is linear or branched $C_1$-$C_{12}$-alkyl, $C_5$-$C_8$-cycloalkyl, phenyl or $C_7$-$C_{10}$-phenalkyl, where cycloalkyl and phenyl may be substituted by $C_1$-$C_4$-alkyl, or

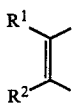

is a fused-on benzene ring which may be substituted by hydroxy, halogen, $C_1$-$C_{12}$-alkyl, $C_1$-$C_{12}$-alkoxy, $C_7$-$C_9$-phenylalkyl, phenyl, —COOR$^6$, —CO—R$^6$, —CO—NH—R$^6$, —COOH, —O—COR$^6$, —NH—CO—R$^6$, —SO$_2$—R$^6$ or —CN, where R$^6$ is linear or branched $C_1$-$C_{12}$-alkyl, $C_5$-$C_8$-cycloalkyl, phenyl or $C_7$-$C_{10}$-phenalkyl and the cycloalkyl and phenyl radicals may be substituted by $C_1$-$C_4$-alkyl, $R^3$ and $R^4$ are each hydrogen or one of the radicals $R^3$ or $R^4$ is $C_1$-$C_4$-alkyl or $C_7$-$C_9$-phenalkyl and, if n is 1, X (a) is phenyl, naphthyl or a 5- or 6-membered aromatic, possibly benzofused, heterocyclic, these radicals being unsubstituted or monosubstituted or disubstituted by $C_1$-$C_{12}$-alkyl, $C_1$-$C_{12}$-alkoxy, methylenedioxy, ethylenedioxy, phenoxy, $C_7$-$C_9$-phenylalkyloxy, $C_7$-$C_9$-phenylalkyl, trifluoromethyl, hydroxyl, halogen, —S—R$^7$, —COR$^7$, —COOR$^7$, —COOH, —CN, —CONH—R$^7$, —NH—R$^7$, —N(R$^7$)$_2$, —O—COR$^7$ or —NH—COR$^7$, where R$^7$ is linear or branched $C_1$-$C_{12}$-alkyl, $C_5$-$C_8$-cycloalkyl, phenyl or $C_7$-$C_{10}$-phenalkyl, in which cycloalkyl and phenyl may be substituted by $C_1$-$C_4$-alkyl, or if n is 2

X (b) is phenylene or naphthylene, these radicals being unsubstituted or substituted by $C_1$—$C_{12}$-alkyl, $C_1$-$C_{12}$-alkoxy or halogen, or (c) a is a radical of the formula

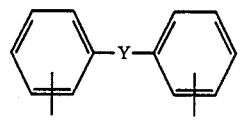

where Y is a radical of the formula —(CH$_2$)$_m$—, —CO—, —CO—(CH$_2$)$_p$CO—, —OCO—(CH$_2$)$_p$COO—, —NH—CO—(CH$_2$)$_p$—CO—NH—, —O—,

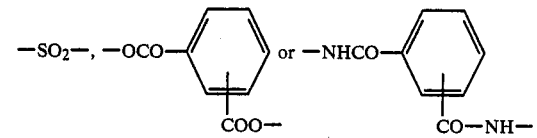

m is 1, 2 or 3, p is 0 or an integer from 1 to 8.

The photostabilized polymers of the invention, if compared with the compounds known from U.S. Pat. Nos. 3,907,700 and 4,011,236, which must be considered closest to those used according to the invention, show a superior action in long-term stabilization, a low volatility, a reduced migration and an enhanced thermostability.

For instance, the compound of Example 12 gives a highly photostabilized polyurethane integral foam. The stabilization obtained hereby is substantially superior to that obtained with prior art stabilizers such as 2-(2'-hydroxy-5'-methylphenyl)benzotriazole, di(1,2,2,6,6-pentamethyl-4-piperidyl)sebacate and/or triethylene glycolbis-3-(3-t-butyl-4-hydroxy-5-methylphenyl)propionate.

Halogen is fluorine, preferably chlorine or bromine.

Suitable hetaryl for $R_1$ and $R^2$ is for example pyridyl, furyl, quinolyl and thiophenyl.

Preferably, $R^1$ and $R^2$ are each phenyl, pyridyl or furyl, these radicals being unsubstituted or substituted by $C_1$-$C_4$-alkyl, $C_1$-$C_4$-alkoxy, chlorine or bromine.

Preference is further given to compounds (I) where

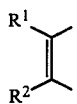

is a fused-on benzene ring which may be substituted as indicated above.

Preferred substituents on the fused-on benzene ring are chlorine, $C_1$-$C_6$-alkyl and $C_1$-$C_8$-alkoxy, such as methyl, ethyl, i-propyl, 2-butyl, tert.-butyl, amyl, hexyl, methoxy, ethoxy, i-propoxy, n-butoxy, pentoxy and hexoxy.

$R^3$ and $R^4$ are each hydrogen or one of the radicals $R^3$ or $R^4$ is $C_1$-$C_4$-alkyl or $C_7$-$C_9$-phenylalkyl, such as methyl, ethyl, n-propyl, n-butyl, benzyl, 2-phenyl-1-ethyl or 2-phenyl-2-propyl. $R^3$ and $R^4$ are preferably each hydrogen.

The meaning of X depends on whether n is 1 or 2.

If n is 1, then X is phenyl, naphthyl or a 5- or 6-membered aromatic, possibly benzofused, heterocyclic, the radicals mentioned being unsubstituted or monosubstituted or disubstituted as stated above. Of these compounds (I) preference is given to those where X is unsubstituted, monosubstituted or disubstituted phenyl.

Preferably X is phenyl substituted by linear or branched $C_1$-$C_{12}$-alkyl, trifluoromethyl, $C_1$-$C_{12}$-alkoxy, methylenedioxy, ethylenedioxy, $C_7$-$C_9$-phenalkyl, phenoxy, phenyl, $C_1$-$C_{12}$-alkoxycarbonyl, $C_1$-$C_{12}$-alkylcarbonyl, benzoyl, cyano, N,N-di-$C_1$-$C_6$-alkylamino, $C_1$-$C_{12}$-alkyl-carbonylamino, $C_1$-$C_{12}$-alkanoyloxy, benzoyloxy, $C_7$-$C_9$-phenalkanoyloxy or chlorine, the number of substituents being 1 or 2.

Specific examples of substituents on the phenyl radical X, in addition to those specified, are:

(α) alkyl such as methyl, ethyl, n- and i-propyl, n-butyl, 2-butyl, tert.-butyl, n-pentyl, tert.-pentyl, n-hexyl, n-heptyl, n-octyl, 2-ethylhexyl, n-nonyl, n-decyl and n-dodecyl;

(β) alkoxy such as methoxy, ethoxy, i-propoxy, n-butoxy, n-pentoxy, i-pentoxy, n-hexoxy, n-heptoxy, n-octoxy, 2-ethylhexoxy, n-nonoxy, n-decoxy and n-dodecoxy;

(γ) phenoxy, benzyloxy, 2-phenylethoxy, 3-phenylpropoxy.

Particular preference is given to compounds (I) where n=1 and where X is 4-$C_1$-$C_{12}$-alkylphenyl, 4-$C_1$-$C_{12}$-alkoxyphenyl, 4-phenoxyphenyl, 4-$C_1$-$C_{12}$-alkylcarbonylaminophenyl or 4-$C_1$-$C_{12}$-alkanoyloxyphenyl.

If n is 2, then X is either (b) unsubstituted or alkyl- or alkoxy-substituted phenylene or naphthylene or (c) a radical of the formula

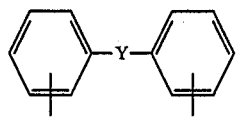

(II)

where Y has the abovementioned meanings. Preferably Y is —$CH_2$—, —O— or —$SO_2$—.

If n is 2, preference is given to compounds (I) where X is unsubstituted or $C_1$-$C_{12}$-alkyl- or $C_1$-$C_{12}$-alkoxy-substituted phenylene or a radical of the formula II, the phenylene radicals in (II) being unsubstituted or substituted by $C_1$-$C_4$-alkyl or $C_1$-$C_4$-alkoxy, although preferably unsubstituted, and Y is —$CH_2$— or —O—.

The present invention also relates to novel imidazole-2-carboxanilides of the formula (III)

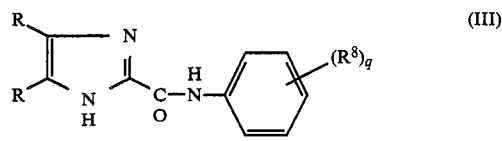

(III)

where the two Rs are each independently of the other

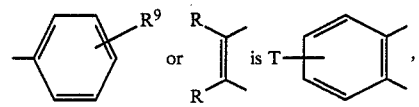

$R^8$ is $C_1$-$C_{12}$-alkyl, $C_1$-$C_{12}$-alkoxy, phenoxy, $C_7$-$C_9$-phenalkoxy, $C_7$-$C_9$-phenalkyl, trifluoromethyl, N,N-di-$C_1$-$C_6$-alkylamino, $C_2$-$C_{12}$-alkanoylamino, $C_1$-$C_{12}$-alkylcarbonyl, $C_1$-$C_{12}$-alkoxycarbonyl, benzoyl, cyano, methylenedioxy or ethylenedioxy, $C_2$-$C_{12}$-alkanoyloxy, benzoyloxy, $C_7$-$C_9$-phenalkanoyloxy, $R^9$ is $C_1$-$C_{12}$-alkyl, $C_1$-$C_4$-alkoxy, chlorine or hydrogen, T is hydrogen, $C_1$-$C_4$-alkyl, $C_1$-$C_4$-alkoxy, trifluoromethyl, phenyl, $C_7$-$C_9$-phenalkyl or chlorine, and q is 1 or 2.

Preferably T is hydrogen, methyl or chlorine.

Of the compounds (III), preference is given to those of the formulae

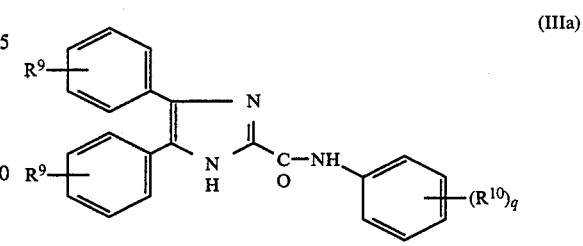

(IIIa)

and

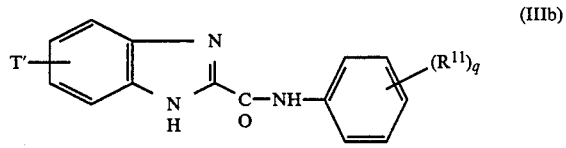

(IIIb)

where
$R^9$ is methyl, methoxy or hydrogen,
$R^{10}$ is $C_1$-$C_6$-alkyl, $C_1$-$C_4$-alkoxy or chlorine,
$R^{11}$ is $C_1$-$C_{12}$-alkyl, $C_1$-$C_{12}$-alkoxy, methylenedioxy, ethylenedioxy, trifluoromethyl, N,N-di-$C_1$-$C_4$-alkylamino, $C_2$-$C_{12}$-acylamino, $C_2$-$C_{12}$-acyloxy, benzoyloxy or $C_7$-$C_9$-phenacyloxy,
T' is hydrogen, Chd 1-$C_4$-alkyl or chlorine, preferably hydrogen, chlorine or methyl, and
q is 1 or 2.

The novel compounds of the formulae (III), (IIIa) and (IIIb) where $R^8$, $R^{10}$ and $R^{11}$ are linear $C_8$-$C_{12}$-alkoxy are highly suitable for stabilizing surface coatings, such as finished coats, and two-layer metallic effect coatings. The addition of these stabilizers substantially improves the performance fastness, in particular the light and weather fastness, of pigmented industrial coatings.

The compounds of the formulae (I), (III), (IIIa) and (IIIb) can be prepared in a conventional manner.

If $R^1$ and $R^2$ in (I) are a fused-on benzene ring, these compounds can be synthesized by condensing an o-phenylenediamine derivative of the formula (V)

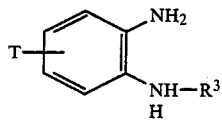

with an ethyl oxamate of the formula VI

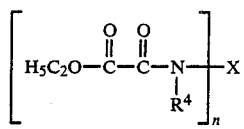

as described in French Pat. No. 1,517,719 and Bull. Soc. Chim. 10 (1966), 3368.

A further method of synthesis comprises reacting benzimidazole-2-carboxylic acid derivatives with aromatic amines:

(i) if $R^8$ is an electron-withdrawing substituent, by reacting the 2-trichlorobenzimidazole derivative (VII)

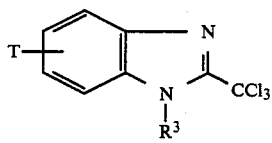

with an aromatic amine of the formula (VIII)

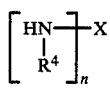

as described in J. Chem. Soc. Sect. C., 1967, 20, and (ii) if $R^8$ is an electron donor substituent, by reacting a dibenzoimidazo(1,2-a,1',2'-d)tetrahydropyrazine-6,13-dione derivative of the formula (IX)

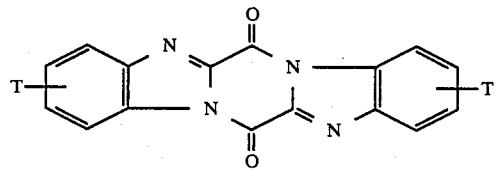

with an aromatic amine of the formula VIII, analogously to the reaction described in Indian J. Chem. 18B (1979), 464.

Furthermore, the compounds of the formula (I) are readily accessible by reacting an imidazole derivative of the formula (X)

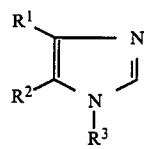

with an aromatic isocyanate of the formula (XI)

The reaction is similar to that described in Chem. Ber. 92 (1959), 550.

The compounds (I), (III), (IIIa) and (IIIb) are incorporated in the polymers in a conventional manner.

For example, the compounds can be incorporated by mixing them with or without further additives into the melt in a conventional manner before or during shaping, or, alternatively, by applying the dissolved or dispersed compounds to the polymer directly or by mixing into a solution, suspension or emulsion of the polymer, and if necessary allowing the solvent to evaporate.

Examples of polymers to be stabilized are: polyolefins, polystyrene, styrene polymers, halogen-containing vinyl polymers, polyacrylates, polymethacrylates, polyacrylamides, polyacrylonitrile, polyvinyl alcohol and acyl derivatives thereof, polyacetates, polyalkylene oxides, polyphenylene oxides, polyurethanes and polyureas, polysulfones, polyamides, polyesters, polycarbonates, crosslinked polymers of aldehydes and phenols, urea and/or melamine, unsaturated polyester resins, alkyd resins, and thermosetting and thermoplastic acrylic resins.

The stabilizers according to the invention are mixed into the polymers individually or mixed in amounts of from 0.01 to 5, preferably from 0.05 to 2.5, in particular from 0.1 to 2, percent by weight, based on the material to be stabilized.

The materials thus stabilized can be converted into the customary application forms, for example films, fibers, ribbons or profiles, or may be used as binders for paints, adhesives, cements or molding compositions.

In practice the compounds of the formula I can be used together with from 0.1 to 5, preferably from 0.5 to 3, % by weight of further customary additives, such as antioxidants, further light stabilizers or mixtures thereof.

Examples of these customary additives are: antioxidants, UV absorbers and light stabilizers such as 2-(2'-hydroxyphenyl)benzotriazole, 2,4-bis(2'-hydroxyphenyl)-6-alkyl-s-triazine, 2-hydroxybenzophenone, 1,3-bis(2'-hydroxybenzoyl)benzenes, esters of substituted or unsubstituted benzoic acids, acrylates, and also nickel compounds, sterically hindered amines, metal deactivators, phosphites, peroxide-destroying compounds, polyamide stabilizers, basic costabilizers, nucleating agents and other additives such as plasticizers, lubricants, emulsifiers, fillers, carbon black, kaolin, talc, glass fibers, pigments, optical brighteners, flame retardants and antistatics.

The compounds of the formula (I) are suitable in particular for stabilizing polyurethanes derived from polyethers, polyesters and polybutadienes having terminal hydroxyl groups and aliphatic or aromatic polyisocyanates, and intermediates thereof, to degradation due to heat and in particular due to light.

An improved stabilizing action is obtained if a known antioxidant, for example a compound based on sterically hindered phenols, or a sulfur- or phosphorus-containing costabilizer is used in addition.

Examples of such phenolic antioxidants are 2,6-di-tert.-butyl-4-methylphenol, n-octadecyl β-(3,5-di-tert.-butyl-4-hydroxyphenyl)propionate, 1,1,3-tris(2'-methyl-4'-hydroxy-5'-tert.-butylphenyl)butane, 1,3,5-trimethyl-2,4,6-tris(3',5'-di-tert.-butyl4'-hydroxybenzyl)-benzene, 1,3,5-tris(3',5'-di-tert.-butyl-4'-hydroxybenzyl)isocyanurate, 1,3,5-tris[3',5'-di-tert.-butyl-4'-hydroxyphenyl)propionyloxyethyl]isocyanurate, 1,3,5-tris(2',6'-di-methyl-3'-hydroxy-4'-tert.-butylbenzyl)isocyanurate, pentaerythritol tetrakis[β-(3,5-di-tert.-butyl-4-hydroxyphenyl)propionate], triethylene glycol bis-3-(3'-t-butyl-4'-hydroxy-5'-methylphenyl)propionate, derivatives of 6-hydroxy-2,5,7,8-tetramethylchroman such as α-tocopherol and (6-hydroxy-2,5,7,8-tetramethylchroman-2-yl)ethyl stearate.

Examples of phosphorus-containing antioxidants are: trisnonylphenyl phosphite, distearyl pentaerythritol diphosphite, tris(2,4-di-tert.-butylphenyl)phosphite, tris(2-tert.-butyl-4-methylphenyl)phosphite, bis(2,4-di-tert.-butylphenyl)pentaerythritol diphosphite and tetrakis(2,4-di-tert.-butylphenyl)4,4'-biphenylene diphosphite.

Examples of sulfur-containing antioxidants are dilauryl thiodipropionate, dimyristyl thiodipropionate, distearyl thiodipropionate, pentaerythritol tetrakis(β-laurylthiopropionate), and pentaerythritol tetrakis(β-hexylthiopropionate).

Particularly good stabilization is obtained by adding to the compounds of the formula (I), (III), (IIIa) and (IIIb) one or more light stabilizers from the class of sterically hindered amines in a customary concentration.

Examples of sterically hindered amines are: bis(2,2,6,6-tetramethylpiperidyl)sebacate, bis(1,2,2,6,6-pentamethylpiperidyl)sebacate, bis(1,2,2,6,6-pentamethylpiperidyl)esters, the condensation product of 1-hydroxyethyl-2,2,6,6-tetramethyl-4-hydroxypiperidine and succinic acid, the condensation product of N,N'-(2,2,6,6-tetramethylpiperidyl)hexamethylenediamine and 4-tert.-octylamino-2,6-dichloro-1,3,5-s-triazine, tris(2,2,6,6-tetramethylpiperidyl)nitrilotriacetate, tetrakis(2,2,6,6-tetramethyl-4-piperidyl)-1,2,3,4-butanetetracarboxylic acid, 1,1'-(1,2-ethanediyl)bis(3,3,5,5-tetramethylpiperazinone), and the condensation products of 4-amino-2,2,6,6-tetramethylpiperidines and tetramethylolacetylenediureas.

Especially good stabilization of polyurethanes is obtained if the polyurethane contains a mixture of one or more compounds of the formula (I), one or more of the abovementiond antioxidants and one or more compounds of a sterically hindered amine. The Examples which follow will additionally explain the invention.

(A) PREPARATION EXAMPLES

EXAMPLE 1

20.7 g (0.1 mol) of ethyl N-(4-methylphenyl)oxamate and 10.8 g (0.1 mol) of o-phenylenediamine are refluxed under nitrogen in 50 ml of dry dimethylformamide for 8 hours. After cooling down, 200 ml of methanol and 140 g of ice are added. The resulting precipitate is filtered off with suction and washed with a 1:1 mixture of methanol and water. Recrystallization from ethanol in the presence of active carbon gives 9.5 g of a colorless product of formula

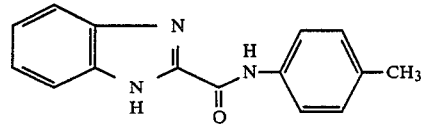

having a melting point of 226°–227° C.

Analysis: $C_{15}H_{13}N_3O$ (251.3). calculated: C 71.69, H 5.21, N 16.72, O 6.37. found: C 71.6, H 5.5, N 16.2, O 7.0.

EXAMPLES 2 TO 11

Practicing procedures analogous to that of Example 1 on appropriate starting materials gives the compounds listed in Table 1.

TABLE 1

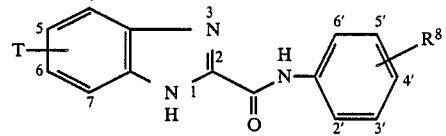

| Example | T | $R^8$ | m.p. [°C.] |
|---|---|---|---|
| 2 | H | 4'-$C_2H_5$ | 219 |
| 3 | H | 2'-$C_2H_5$ | 200 |
| 4 | H | 4'-i-$C_3H_7$ | 222 |
| 5 | H | 4'-t-$C_4H_9$ | 235 |
| 6 | H | 2',5'-(t-$C_4H_9$)$_2$ | 224–226 |
| 7 | H | 2'-$OC_2H_5$ | 219–220 |
| 8 | 5/6-$CH_3$* | 4'-t-$C_4H_9$ | 211–213 |
| 9 | 5/6-$CH_3$* | 4'-i-$C_3H_7$ | 247–249 |
| 10 | 5/6-$CH_3$* | 2',5'-($OC_2H_5$)$_2$ | 212–215 |
| 11 | 5/6-$CH_3$* | 4'-$CO_2C_2H_5$ | 207–208 |

*Mixture of 5- and 6-methyl compound

EXAMPLE 12

14.4 g (0.05 mol) of dibenzimidazo(1,2a,1',2'-d)tetrahydropyrazine-6,13-dione and 14.8 g (0.11 mol) of p-phenetidine are heated under reflux in 80 ml of dimethylformamide for 3.5 hours. After dilution with 300 ml of methanol the precipitated product is filtered off with suction and washed with methanol to give 18.0 g of the benzimidazole-2-carboxanilide of the formula

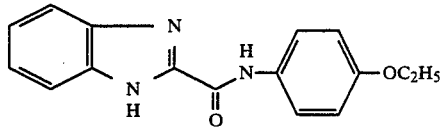

Melting point 201°–202° C.

Analysis: $C_{16}H_{15}N_3O_2$ (281.21). calculated: C 68.31, H 5.37, N 14.94, O 11.37. found: C 68.2, H 5.5, N 14.9, O 11.3.

EXAMPLES 13 TO 32

Practicing procedures analogous to that of Example 12 on appropriate starting materials gives the compounds mentioned in Table 2.

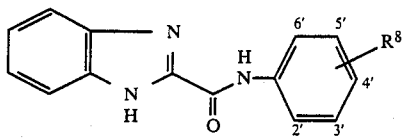

| Example | R⁸ | m.p. [°C.] |
|---|---|---|
| 13 | 4'-OCH$_3$ | 237–239 |
| 14 | 3'-OC$_2$H$_5$ | 211–213 |
| 15 | 4'-OC$_4$H$_9$—n | 163–165 |
| 16 | 4'-OC$_6$H$_{13}$—n | 151–153 |
| 17 | 4'-OC$_8$H$_{17}$—n | 143–145 |
| 18 | 4'-OC$_{12}$H$_{25}$—n | 141–142 |
| 19 | 2',5'-(OC$_2$H$_5$)$_2$ | 243–244 |
| 20 | 3',4'-O—CH$_2$—O | 262–264 |
| 21 | 3',4'-O—(CH$_2$)$_2$—O— | 268–270 |
| 22 | 4'-C$_{10}$H$_{21}$—n | 140–141 |
| 23 | 4'-C$_{12}$H$_{25}$—n | 130–131 |
| 24 | 4'-N(CH$_3$)$_2$ | 253–254 |
| 25 | 3'-CF$_3$ | 203 |
| 26 | 4'-NHCOCH$_3$ | 308 |
| 27 | 2'-OC$_4$H$_9$—n | 183–184 |
| 28 | 2'-OC$_6$H$_{13}$—n | 175–176 |
| 29 | 2'-OC$_8$H$_{17}$—n | 160–163 |
| 30 | 2'-OC$_{12}$H$_{25}$—n | 145–146 |
| 31 | 4'-OC$_6$H$_5$ | 237–239 |
| 32 | 3',4'-(OCH$_3$)$_2$ | 209 |

EXAMPLE 33

23.6 g (0.1 mol) of 2-trichloromethylenzimidazole and 19.7 g (0.1 mol) of 4-aminobenzophenone are heated under reflux in 220 g of 14% strength hydrochloric acid for 5 hours. After cooling down, the precipitated product is filtered off with suction and washed with acetone. The residue is dissolved in 800 ml of ethanol and 50 ml of 20% strength sodium hydroxide solution, and the solution is then poured onto 2 l of ice-water. The precipitated solid is filtered off with suction and washed neutral with water. Drying leaves 17.6 g of colorless product of the formula

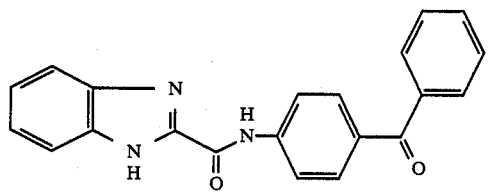

Melting point 230°–231° C.

Analysis: C$_{21}$H$_{15}$N$_3$O$_2$ (341.37). calculated: C 73.89, H 4.42, N 12.31, O 9.37. found: C 73.9, H 4.3, N 12.1, O 9.4.

EXAMPLES 34 TO 37

The compounds indicated in Table 3 were prepared by procedues analogous to that of Example 33.

TABLE 3

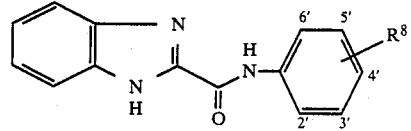

| Example | R⁸ | m.p. [°C.] |
|---|---|---|
| 34 | 2'-COC$_6$H$_5$ | 250–252 |
| 35 | 4'-CO$_2$C$_2$H$_5$ | 214–215 |
| 36 | 4'-CN | 302–303 |
| 37 | 2',4'-(Cl)$_2$ | 304 |

EXAMPLE 38

11.8 g (0.1 mol) of benzimidazole and 21 g (0.12 mol) of 4-n-butylphenyl isocyanate were heated under reflux in 180 ml of dry nitrobenzene for 6 hours. Cooling down resulted in the formation of a precipitate, which was filtered off with suction and washed with nitrobenzene and methanol to give 20.5 g of a colorless solid of the formula

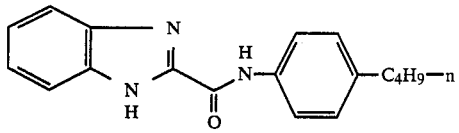

Melting point 205°–206° C.

Analysis: C$_{18}$H$_{19}$N$_3$O (293.4). calculated: C 73.69, H 6.53, N 14.32, O 5.45. found: C 73.9, H 6.8, N 14.1, O 5.5.

EXAMPLES 39 TO 71

Practicing procedures analogous to that of Example 38 on the imidazoles and isocyanates indicated in Table 4 gave the corresponding imidazole-2-carboxanilines.

TABLE 4

| Example | Imidazole derivative | Isocyanate | Melting point [°C.] |
|---|---|---|---|
| 39 | benzimidazole | 2,6-dimethylphenyl isocyanate | 230–231 |
| 40 | benzimidazole | 2,6-diisopropylphenyl isocyanate | 264–265 |

TABLE 4-continued
| Example | Imidazole derivative | Isocyanate | Melting point [°C.] |
|---|---|---|---|
| 41 | 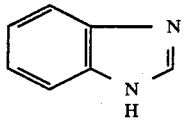 | 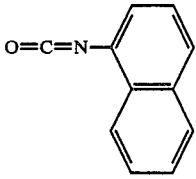 | 282-285 |
| 42 | 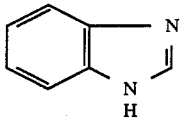 | 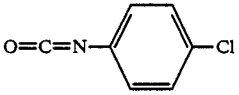 | 248-250 |
| 43 | 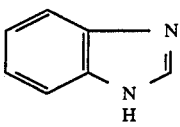 | 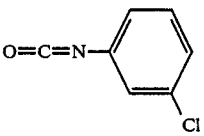 | 244 |
| 44 | 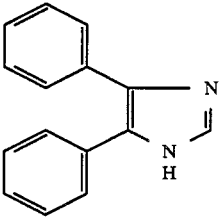 | 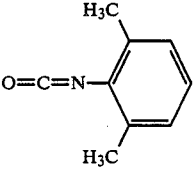 | 264 |
| 45 | 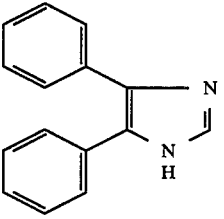 | 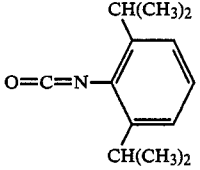 | 290-292 |
| 46 | 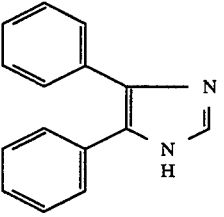 | 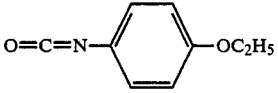 | 223 |
| 47 | 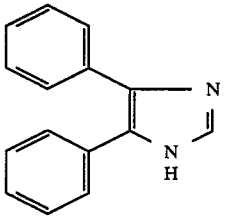 | 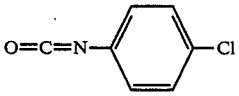 | 237-239 |

TABLE 4-continued

| Example | Imidazole derivative | Isocyanate | Melting point [°C.] |
|---|---|---|---|
| 48 | 4,5-diphenyl-1H-imidazole | 3-chlorophenyl isocyanate | 186–189 |
| 49 | benzimidazole | 4,4'-methylenebis(phenyl isocyanate) | 327 |
| 50 | benzimidazole | 2,4-tolylene diisocyanate | 350 (dec.) |
| 51 | 4,5-bis(4-methoxyphenyl)-1H-imidazole | phenyl isocyanate | 236–238 |
| 52 | 4,5-bis(4-methoxyphenyl)-1H-imidazole | 4-ethoxyphenyl isocyanate | 197–198 |
| 53 | 4,5-bis(4-methoxyphenyl)-1H-imidazole | 4-chlorophenyl isocyanate | 233–235 |
| 54 | 4,5-bis(4-methoxyphenyl)-1H-imidazole | 4-(ethoxycarbonyl)phenyl isocyanate | 237–240 |

TABLE 4-continued
| Example | Imidazole derivative | Isocyanate | Melting point [°C.] |
|---|---|---|---|
| 55 | 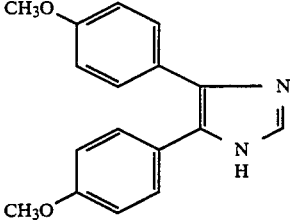 | 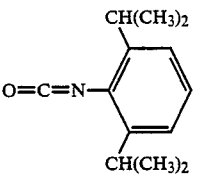 | 244–246 |
| 56 | 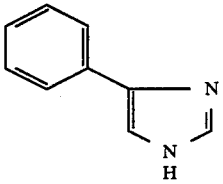 | 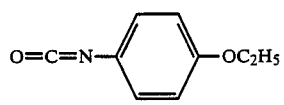 | 158–160 |
| 57 | 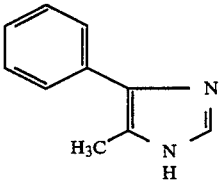 | 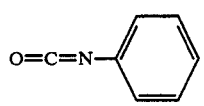 | 217–218 |
| 58 | 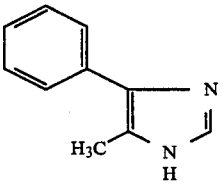 | 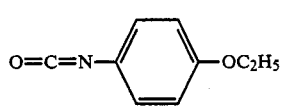 | 192 |
| 59 | 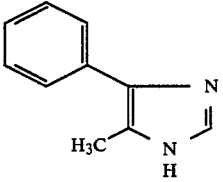 | 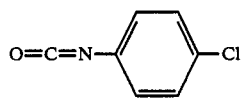 | 238–240 |
| 60 | 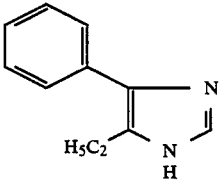 | 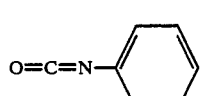 | 157–158 |
| 61 | 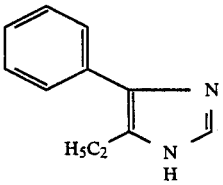 | 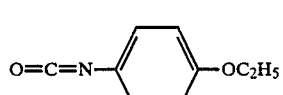 | 170–172 |

TABLE 4-continued

| Example | Imidazole derivative | Isocyanate | Melting point [°C.] |
|---|---|---|---|
| 62 | 4-phenyl-5-ethyl-imidazole | O=C=N—C6H4—Cl (4-chloro) | 180–181 |
| 63 | 5,6-dimethylbenzimidazole | O=C=N—C6H5 | 299 |
| 64 | 5,6-dimethylbenzimidazole | O=C=N—C6H4—OC2H5 (4-ethoxy) | 272 |
| 65 | 5,6-dimethylbenzimidazole | O=C=N—C6H4—Cl (4-chloro) | 286 |
| 66 | 5-ethoxybenzimidazole | O=C=N—C6H5 | 210–212 |
| 67 | 5-ethoxybenzimidazole | O=C=N—C6H4—OC2H5 (4-ethoxy) | 212 |
| 68 | 5-ethoxybenzimidazole | O=C=N—C6H4—Cl (4-chloro) | 228–229 |
| 69 | 5-(2,2-diphenyl-propyl)-benzimidazole (H3C-C(C6H5)(CH3)-) | O=C=N—C6H4—Cl (4-chloro) | 103 |
| 70 | 5-(2,2-diphenyl-propyl)-benzimidazole | O=C=N—C6H4—OC2H5 (4-ethoxy) | 207–209 |
| 71 | 5-(2,2-diphenyl-propyl)-benzimidazole | O=C=N—C6H4—Cl (4-chloro) | 205–206 |

EXAMPLE 72

14.4 g (0.05 mol) of dibenzimidazo(1,2a,1',2'-d)tetrahydropyrazine-6,13-dione and 30 g (0.18 mol) of 4-propionylaminoaniline are heated under reflux in 70 ml of dry dimethylformamide for 3 hours. After cooling down, about 700 ml of methanol are added. The precipitated solid is filtered off with suction and washed with methanol and dried to leave 20.7 g of the benzimidazole-2-carboxanilide of the formula

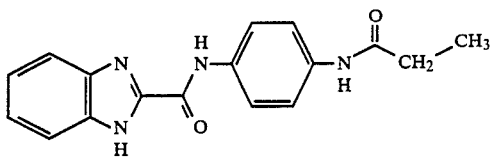

Melting point 289°–291° C.
Analysis: $C_{17}H_{16}N_4O_2$ (308.34). calculated: C 66.22, H 5.23, N 18.17, O 10.38. found: C 66.4, H 5.3, N 17.8, O 10.5.

EXAMPLES 73 TO 84

Practicing procedures analogous to that of Example 72 on appropriate starting materials gives the compounds indicated in Table 5.

TABLE 5

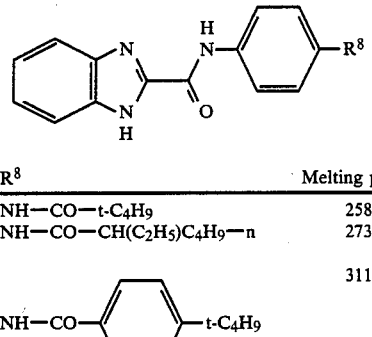

| Example | R⁸ | Melting point [°C.] |
|---|---|---|
| 73 | NH—CO—t-$C_4H_9$ | 258–260 |
| 74 | NH—CO—CH($C_2H_5$)$C_4H_9$—n | 273–274 |
| 75 | NH—CO—⟨C₆H₄⟩—t-$C_4H_9$ | 311–313 |
| 76 | $OC_5H_{11}$—n | 200 |
| 77 | $OC_5H_{11}$—i | 220 |
| 78 | $OC_7H_{15}$—n | 160 |
| 79 | $OCH_2$—CH($C_2H_5$)$C_4H_9$—n | 140 |
| 80 | $OC_9H_{19}$—n | 150 |
| 81 | $OC_{10}H_{21}$—n | 145 |
| 82 | $OCH_2$—$C_6H_5$ | 217 |
| 83 | $OCH_2$—$CH_2$—$C_6H_5$ | 194 |
| 84 | OH | 328–330 |

EXAMPLE 85

7.8 g (0.065 mol) of pivaloyl chloride are added dropwise at from 25° to 50° C. to a solution of 12.7 g (0.05 mol) of 4'-hydroxybenzimidazole-2-carboxanilide (from Example 78) in 50 ml of dry pyridine and stirred in at 50° C. for 3 hours. The reaction solution is poured onto 300 ml of ice-water and 100 ml of concentrated hydrochloric acid and stirred in for 20 minutes. The precipitated solid is filtered off with suction and washed with water. Recrystallization from toluene gives 9.5 g of a colorless product of the formula

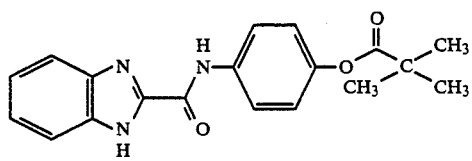

Melting point 266°–267° C.
Analysis: $C_{19}H_{19}N_3O_3$ (337.38). calculated: C 67.64, H 5.68, N 12.45, O 14.22. found: C 67.8, H 5.8, N 12.2, O 14.1.

EXAMPLES 86 TO 89

Procedures analogous to that of Example 85 gave the compounds listed in Table 6.

TABLE 6

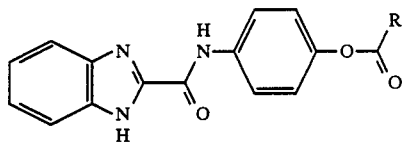

| Example | R | m.p. [°C.] |
|---|---|---|
| 86 | $C_2H_5$ | 227–229 |
| 87 | CH($C_2H_5$)$C_4H_9$—n | 154 |
| 88 | $C_9H_{19}$ (mixed isomers) | 135–137 |
| 89 | ⟨C₆H₅⟩—$C_4H_9$—t | 281–283 |

EXAMPLE 90

9.0 g of methyl iodide are added dropwise at room temperature to a suspension of 8.45 g (0.03 mol) of 4'-ethoxybenzimidazole-2-carboxanilide (from Example 12) and 2.3 g of potassium hydroxide in 90 ml of anhydrous ethanol in the course of 30 minutes. The reaction mixture is stirred at room temperature for 24 hours and poured onto 300 ml of water, the resulting mixture is filtered with suction, and the filter residue is thoroughly washed with water. 8.2 g of a colorless product of the formula

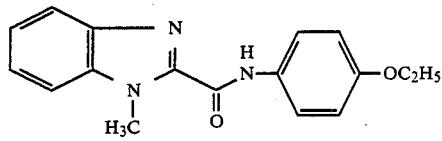

having a melting point of 151° C. are isolated.
Analysis: $C_{17}H_{17}N_3O_2$ (295.34). calculated: C 69.15, H 5.77, N 14.24, O 10.84. found: C 69.3, H 5.8, N 14.3, O 10.8.

EXAMPLE 91

5.5 g of potassium hydrogencarbonate and 7.1 g of 1-bromopropane are added to a solution of 14.1 g (0.05 mol) of 4'-ethoxybenzimidazole-2-carboxanilide (from Example 12) in 250 ml of dry dimethylformamide and stirred in at from 80° to 85° C. for 16 hours. The reaction mixture is filtered hot, the filter residue is washed with from 20 to 30 ml of dimethylformamide, and the solvent is drawn off in a rotary evaporator. The residue is dissolved in 100 ml of methanol by heating, and the solution is treated with active carbon, which is then filtered off. Cooling gives a crystalline precipitate of 12.7 g of a colorless solid of the formula

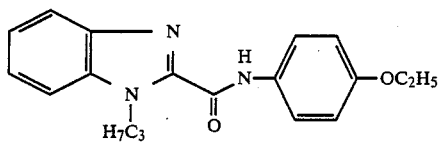

Melting point 96°–97° C.

Analysis: $C_{19}H_{21}N_3O_2$ (323.40). calculated: C 70.59, H 6.50, N 13.0, O 9.91. found: C 70.1, H 6.7, N 12.9, O 10.0.

EXAMPLE 92

Example 91 is repeated, except that benzyl bromide is used in place of 1-bromopropane, affording the following product of the formula

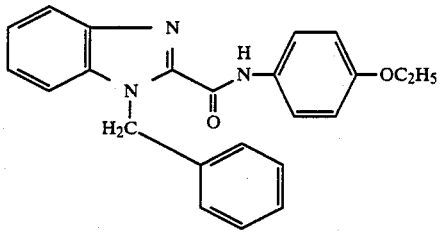

Melting point: 157°–159° C.

Analysis: $C_{23}H_{21}N_3O_2$ (371.44). calculated: C 74.39, H 5.67, N 11.32, O 8.62. found: C 74.1, H 5.7, N 11.5, O 9.0.

(B) APPLICATION EXAMPLES

EXAMPLE 93

(Photostabilizing action in polyurethane)

The stabilizers listed in Table 7 are dissolved at 40°–50° C. in 150 g of polyetherol by stirring. The solution is intimately mixed with 76.5 g of a diphenylmethane diisocyanate formulation by stirring at 1,000 r.p.m. for 10–15 seconds. The mixture is immediately poured into a sealable mold, which has been preheated to 50° C., and is left for curing in the sealed state for 3–4 minutes.

Testing is carried out on foam sections having a continuous surface. The samples are exposed in a Xenotest® 1200 and assessed for yellowness in terms of the yellowness index (YI) as defined in ASTM D 1925. The results are given in Table 7, columns 3 to 6.

TABLE 7

| Stabilizer | Concentration [%] | YI 0 h | acc. to ASTM D 1925 24 h | 48 h | 72 h |
|---|---|---|---|---|---|
| 7.1 Control | — | 10.0 | 55.0 | 66.0 | 73.0 |
| 7.2 Compound of Ex. 3 | 1.0 | 15.3 | 40.4 | 52.6 | 65.0 |
| 7.3 Compound of Ex. 2 | 1.0 | 13.9 | 37.2 | 46.8 | 56.4 |
| 7.4 Compound of Ex. 4 | 1.0 | 14.4 | 34.2 | 43.5 | 54.8 |
| 7.5 Compound of Ex. 12 | 1.0 | 11.5 | 27.5 | 38.2 | 50.7 |
| 7.6 Compound of Ex. 12 + A* + B** | 0.5 0.5 0.5 | 10.0 | 30.1 | 37.2 | 46.8 |
| 7.7 Compound of Ex. 12 | 0.5 | | | | |

TABLE 7-continued

Cycle in Xenotest 1200: 17 min exposure to light
3 min exposure to water spray
Temperature 45° C.

| Stabilizer | Concentration [%] | YI 0 h | acc. to ASTM D 1925 24 h | 48 h | 72 h |
|---|---|---|---|---|---|
| + A* Triethylene glycol bsi-3-(3-t-butyl-4-hydroxy-5-methyl-phenyl) propionate | 0.5 0.5 | 11.0 | 26.5 | 29.5 | 41.5 |
| 7.8 2-(2'-Hydroxy-5'-methylphenyl)benzo-triazole | 0.5 | | | | |
| + C*** + Triethylene glycol bis-3-(3-t-butyl-4-hydroxy-5-methylphenyl) propionate | 0.5 0.5 | 12.2 | 32.3 | 42.0 | 48.5 |

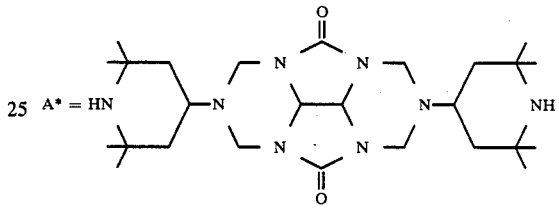

B** = Mixture of 1 part by weight of α-tocopherol + 10 parts by weight of tris(nonylphenyl) phosphite

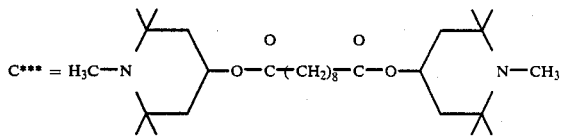

EXAMPLE 94

The samples listed below in Table 8, which were prepared analogously to the method described in Example 93, were exposed in a Xenotest® 450 for 48 hours and assessed for yellowness in terms of the yellowness index as defined in ASTM D 1925.

TABLE 8

| stabilizer | Conc. (% by wt.) | Yellowness index according to ASTM D 1925 in Xenotest 450 after 0 h | 48 h |
|---|---|---|---|
| 8.1 Control | — | 1.72 | 47.91 |
| 8.2 Compound of Ex. 13 | 1 | 5.79 | 20.81 |
| 8.3 Compound of Ex. 12 | 1 | 1.91 | 18.23 |
| 8.4 Compound of Ex. 15 | 1 | 3.59 | 19.15 |
| 8.5 Compound of Ex. 16 | 1 | 2.89 | 12.88 |
| 8.6 Compound of Ex. 17 | 1 | 5.11 | 21.11 |
| 8.7 Compound of Ex. 14 | 1 | 10.04 | 26.76 |
| 8.8 Compound of Ex. 23 | 1 | 6.58 | 21.68 |

EXAMPLE 95

The procedure of Example 94 was used to test the following stabilizer combinations listed in Table 9 in PUR foam systems.

TABLE 9

Xenotest ® 450

| | Stabilizer | Conc. (% by wt.) | Yellowness index according to ASTM D 1925 in Xenotest 450 after 0 h | 48 h |
|---|---|---|---|---|
| 9.1 | Control | — | 3.84 | 24.77 |
| 9.2 | Compound of Ex. 12 | 0.5 | | |
| | + A[1] | 0.5 | 4.01 | 13.83 |
| | + B[1] | 0.25 | | |
| 9.3 | 2-(2'-Hydroxy-5'-methylphenyl)benzotriazole | 0.5 | | |
| | + A[1] | 0.5 | 5.52 | 16.23 |
| | + B[1] | 0.25 | | |
| 9.4 | 2-(2'-Hydroxy-5'-methylphenyl)benzotriazole | 0.5 | | |
| | + C[1] | 0.5 | 5.44 | 17.21 |
| | + Triethylene glycol bsi-3-(3-t-butyl-4-hydroxy-5-methylphenyl)propionate | 0.25 | | |
| 9.5 | Compound of Ex. 16 | 0.5 | | |
| | + A[1] | 0.5 | 5.35 | 15.28 |
| | + B[1] | 0.25 | | |
| 9.6 | Compound of Ex. 38 | 0.5 | | |
| | + A[1] | 0.5 | 5.19 | 15.40 |
| | + B[1] | 0.25 | | |
| 9.7 | Compound of Ex. 12 | 0.5 | | |
| | + D[2] | 0.5 | 3.89 | 13.56 |
| | + B[1] | 0.25 | | |
| 9.8 | Compound of Ex. 12 | 0.5 | | |
| | + E[2] | 0.5 | 3.45 | 12.59 |
| | + B[1] | 0.25 | | |

[1]A, B and C are as defined in Example 93

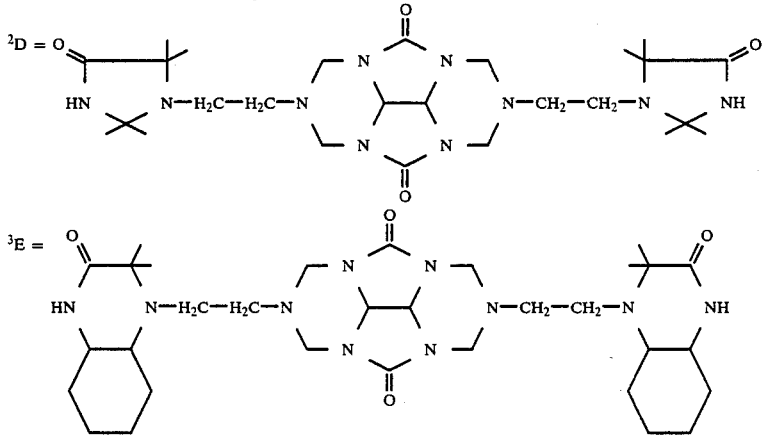

[2]D = (structure shown)

[3]E = (structure shown)

EXAMPLE 96

The series of test results below relates to further stabilizer mixtures prepared in PUR foam systems and exposed in a Xenotest ® 450 for 48 hours.

TABLE 10

| | Stabilizer mixture | Conc. (% by wt.) | Yellowness index according to ASTM D 1925 in Xenotest 450 after 0 h | 48 h |
|---|---|---|---|---|
| 10.1 | Control | — | 5.41 | 42.60 |
| 10.2 | Compound of Ex. 12 | 0.5 | | |
| | + A[1] | 0.5 | 6.71 | 21.49 |
| | + B[1] | 0.25 | | |
| 10.3 | F[3] | 0.5 | | |
| | + A[1] | 0.5 | 6.27 | 27.46 |
| | + B[1] | 0.25 | | |
| 10.4 | Compound of Ex. 12 | 0.5 | | |
| | + G[4] | 0.5 | 7.35 | 19.64 |
| | + B[1] | 0.25 | | |
| 10.5 | Compound of Ex. 12 | 0.5 | | |
| | + H[5] | 0.5 | 7.60 | 22.51 |

TABLE 10-continued

| Stabilizer mixture | Conc. (% by wt.) | Yellowness index according to ASTM D 1925 in Xenotest 450 after | |
|---|---|---|---|
| | | 0 h | 48 h |
| + B[1] | 0.25 | | |

[1]A and B are as defined in Example 93

[3]F = 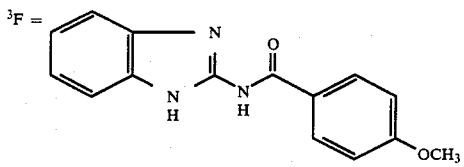

Comparison with U.S. Pat. No. 3,907,700 and 4,011,236

[4]G = 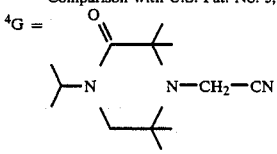

[5]H = 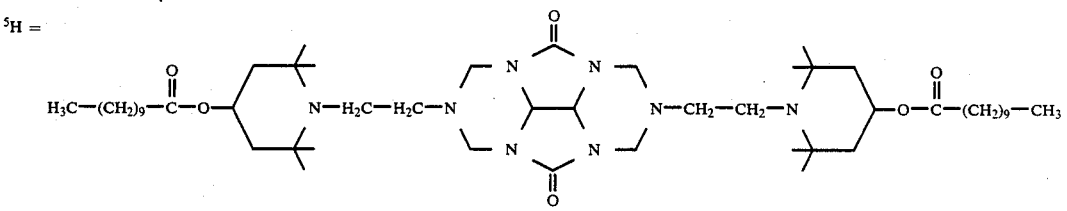

EXAMPLE 97

The samples listed in table 11 were prepared analogously to Example 93 and exposed in a Xenotest ® 450 for 96 hours.

TABLE 11

| Stabilizer mixture | Conc. (% by wt.) | Yellowness index according to ASTM D 1925 in Xenotest 450 after | | |
|---|---|---|---|---|
| | | 0 h | 48 h | 96 h |
| 11.1 Control | — | 1.4 | 24.1 | 31.7 |
| 11.2 2-(2'-Hydroxy-5'-methylphenyl)-benzotriazole | 0.5 | | | |
| +Triethylene glycol bis-3-(3-t-butyl)-4-hydroxy-5-methyl-phenyl propionate | 0.5 | 2.7 | 14.7 | 23.2 |
| 11.3 C[1] | 0.5 | | | |
| +Compound of Ex. 91 | 1.0 | 3.3 | 10.2 | 16.6 |
| +Compound of Ex. 92 | 1.0 | 4.2 | 12.3 | 19.7 |

[1]Example 93: C

We claim:
1. A photostabilized polymer containing as photostabilizer one or more compounds of the formula

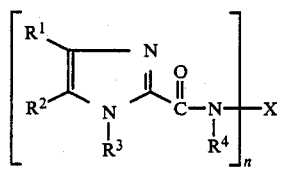 (I)

where
n is 1 or 2,
R[1] and R[2] or one of the radicals R[1] or R[2] are each independently of the other phenyl, pyridyl, furyl, quinolyl or thiophenyl, which each are unsubstituted or substituted by $C_1$-$C_{12}$-alkyl, $C_1$-$C_{12}$-alkoxy, phenoxy, halogen or trifluoromethyl, and the other of the radicals R[1] or R[2] is hydrogen, $C_1$-$C_{12}$-alkyl, $C_7$-$C_9$-phenalkyl or —COOR[5], where R[5] is linear or branched $C_1$-$C_{12}$-alkyl, $C_5$-$C_8$-cycloalkyl, phenyl or $C_7$-$C_{10}$-phenalkyl, where cycloalkyl and phenyl are unsubstituted or substituted by $C_1$-$C_4$-alkyl, or

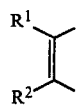

is a fused-on benzene ring which is unsubstituted or substituted by hydroxyl, halogen, $C_1$-$C_{12}$-alkyl, $C_1$-$C_{12}$-alkoxy, $C_7$-$C_9$-phenylalkyl, phenyl, —COOR[6], —CO—R[6], —CO—NH—R[6], —COOH, —O—COR[6], —NH—CO—R[6], —SO$_2$—R[6] or —CN, where R[6] is linear or branched $C_1$-$C_{12}$-alkyl, $C_5$-$C_8$-cycloalkyl, phenyl or $C_7$-$C_{10}$-phenalkyl and the cycloalkyl and phenyl radicals are unsubstituted or substituted by $C_1$-$C_4$-alkyl,
R[3] and R[4] are each hydrogen or one of the radicals R[3] or R[4] is $C_1$-$C_4$-alkyl or $C_7$-$C_9$-phenalkyl and,
if n is 1,
X (a) is phenyl, naphthyl or a 5- or 6-membered aromatic heterocyclic which may be benzofused, these radicals being unsubstituted or monosubstituted or disubstituted by $C_1$-$C_{12}$-alkyl, $C_1$-$C_{12}$-alkoxy, methylenedioxy, ethylenedioxy, phenoxy, $C_7$-$C_9$-phenylalkoxy, $C_7$-$C_9$-phenylalkyl, trifluoromethyl, hydroxyl, halogen, —S—R[7], —COR[7], —COOR[7], OCOR[7], —COOH, —CN, —CONH—R[7], —NH—R[7], —N(R[7])$_2$ or —NH—COR[7], where R[7] is linear or branched $C_1$-$C_{12}$-alkyl, $C_5$-$C_8$-cycloalkyl, phenyl or $C_7$-$C_{10}$-phenalkyl, in which cycloalkyl and phenyl are unsubstituted or substituted by $C_1$-$C_4$-alkyl, or if n is 2

X (b) is phenylene or naphthylene, these radicals being unsubstituted or substituted by $C_1$-$C_{12}$-alkyl, $C_1$-$C_{12}$-alkoxy or halogen, or (c) is a radical of the formula

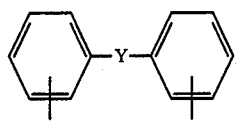

where Y is a radical of the formula —(CH$_2$)$_m$—, —CO—, —CO—(CH$_2$)$_p$CO—, —OCO—(CH$_2$)$_p$COO—, —NH—CO—(CH$_2$)$_p$—CO—NH—, —O—, —SO$_2$—, —OCO— 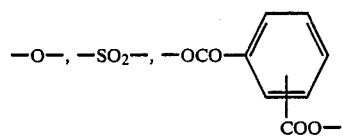 COO— or

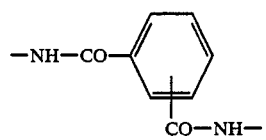

m is 1, 2 or 3, p is 0 or an integer from 1 to 8.

2. A stabilized polymer as claimed in claim 1, wherein, in the formula, X is phenyl which is monosubstituted or disubstituted by $C_1$-$C_{12}$-alkyl, trifluoromethyl, $C_1$-$C_{12}$-alkoxy, methylenedioxy, ethylenedioxy, $C_7$-$C_9$-phenylalkyl, phenoxy, phenyl, $C_1$-$C_{12}$-alkoxycarbonyl, $C_1$-$C_{12}$-alkylcarbonyl, benzoyl, cyano, N,N-di-$C_1$-$C_8$-alkylamino, $C_1$-$C_{12}$-alkylcarbonylamino, $C_1$-$C_{12}$-alkanoyloxy, benzoyloxy, $C_7$-$C_9$-phenylalkanoyloxy or chlorine.

3. A stabilized polymer as claimed in claim 1, which contains as photostabilizer one or more compounds of the formula

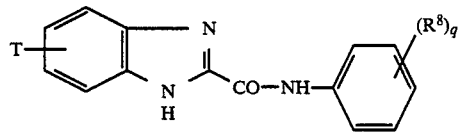

where

T is hydrogen, $C_1$-$C_4$-alkyl, $C_1$-$C_4$-alkoxy, trifluoromethyl, phenyl, $C_7$-$C_9$-phenalkyl or chlorine, $R^8$ is $C_1$-$C_{12}$-alkyl, $C_1$-$C_{12}$-alkoxy, phenoxy, $C_7$-$C_9$-phenalkoxy, $C_7$-$C_9$-phenalkyl, trifluoromethyl, N,N-di-$C_1$-$C_6$-alkylamino, $C_2$-$C_{12}$-alkanoylamino, $C_2$-$C_{12}$-alkanoyloxy, benzoyloxy, $C_7$-$C_9$-phenalkanoyloxy, $C_1$-$C_{12}$-alkylcarbonyl, $C_1$-$C_{12}$-alkoxycarbonyl, benzoyl, cyano, methylenedioxy or ethylenedioxy, and q is 1 or 2.

4. A stabilized polymer as claimed in claim 3, where, in the formula,

T is hydrogen, methyl or chlorine, $R^8$ is $C_1$-$C_{12}$-alkyl, $C_1$-$C_{12}$-alkoxy, methylenedioxy, ethylenedioxy, trifluoromethyl or $C_2$-$C_{12}$-alkanoylamino and q is 1 or 2.

5. A stabilized polymer as claimed in claim 1, wherein the polymer is a polyurethane.

6. A stabilized polymer as claimed in claim 2, wherein the polymer is a polyurethane.

7. A stabilized polymer as claimed in claim 3, wherein the polymer is a polyurethane.

8. A stabilized polymer as claimed in claim 4, wherein the polymer is a polyurethane.

9. A photostabilized polymer containing as photostabilizer one or more compounds of the formula

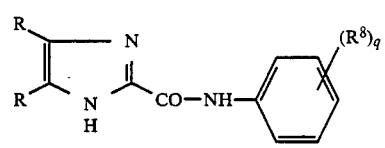

where the two Rs are each independently of the other

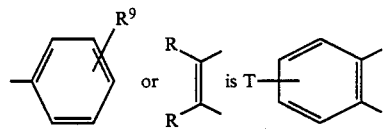 or 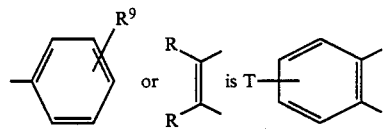

$R^8$ is $C_1$-$C_{12}$-alkyl, $C_1$-$C_{12}$-alkoxy, phenoxy, $C_7$-$C_9$-phenalkoxy, $C_7$-$C_9$-phenalkyl, trifluoro-methyl, N,N-di-$C_1$-$C_6$-alkylamino, $C_2$-$C_{12}$-alkanoylamino, $C_1$-$C_{12}$-alkylcarbonyl, $C_2$-$C_{12}$-alkanoyloxy, benzoyloxy, $C_7$-$C_9$-phenalkanoyloxy, $C_1$-$C_{12}$-alkoxycarbonyl, benzoyl, cyano, methylenedioxy or ethylenedioxy, $R^9$ is $C_1$-$C_{12}$-alkyl, $C_1$-$C_4$-alkoxy, chlorine or hydrogen, T is hydrogen, $C_1$-$C_4$-alkyl, $C_1$-$C_4$-alkoxy, trifluoromethyl, phenyl, $C_7$-$C_9$-phenalkyl or chlorine, and q is 1 or 2.

10. A stabilized polymer as claimed in claim 9, which contains as photostabilizer one or more compounds of the formula

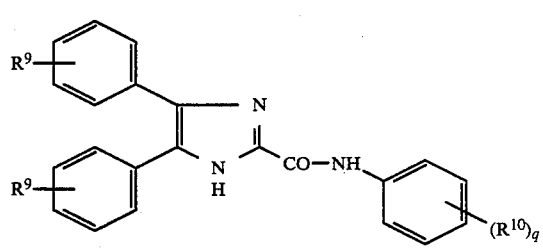

where $R^9$ is methyl, methoxy or hydrogen, $R^{10}$ is $C_1$-$C_{12}$-alkyl, $C_1$-$C_{12}$-alkoxy or chlorine, and q is 1 or 2.

11. A stabilized polymer as claimed in claim 9, which contains as photostabilizer one or more compounds of the formula

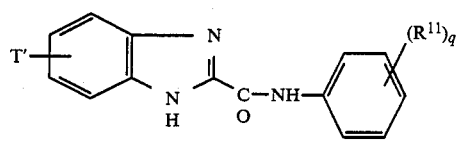
where
T' is hydrogen, methyl or chlorine,
$R^{11}$ is $C_1$-$C_{12}$-alkyl, $C_1$-$C_{12}$-alkoxy, methylenedioxy, ethylenedioxy, trifluoromethyl, N,N-di-$C_1$-$C_4$-alkylamino, $C_2$-$C_{12}$-acylamino, $C_2$-$C_{12}$-alkanoyloxy, benzoyloxy or $C_7$-$C_9$-phenalkanoyloxy, and
q is 1 or 2.
* * * * *